United States Patent [19]

Vedage

[11] Patent Number: 5,444,170
[45] Date of Patent: Aug. 22, 1995

[54] HYDROGENATION OF ACETYLENIC COMPOUNDS

[75] Inventor: Gamini A. Vedage, Bethlehem, Pa.

[73] Assignee: Air Products and Chemicals, Inc., Allentown, Pa.

[21] Appl. No.: 179,466

[22] Filed: Jan. 10, 1994

[51] Int. Cl.$^6$ ............................................. C07C 31/18
[52] U.S. Cl. ................... 568/861; 568/903; 568/618; 568/619; 568/620
[58] Field of Search ............... 568/861, 903, 618, 619, 568/620

[56] References Cited

U.S. PATENT DOCUMENTS

| | | | |
|---|---|---|---|
| 2,359,759 | 10/1944 | Hebbard et al. | 260/677 |
| 3,098,882 | 7/1963 | Arnold | 260/677 |
| 4,228,312 | 10/1980 | Noltes et al. | 585/250 |
| 4,367,353 | 1/1983 | Inglis | 585/258 |
| 4,404,124 | 9/1983 | Johnson et al. | 252/466 |
| 4,831,200 | 5/1989 | Debras et al. | 585/259 |
| 4,864,066 | 9/1989 | Mueller et al. | 568/861 |

*Primary Examiner*—Johann Richter
*Attorney, Agent, or Firm*—Russell L. Brewer; William F. Marsh

[57] ABSTRACT

This invention pertains to an improved process for the hydrogenation of acetylenic compounds prepared by the condensation of ketones or aldehydes with acetylene wherein the acetylenic compounds are contacted with hydrogen in the presence of a hydrogenation catalyst under conditions for effecting hydrogenation. The improvement in the process resides in utilizing a novel cocatalyst system for hydrogenating the acetylenic compounds to paraffins. The cocatalyst converts the inhibiting impurity in the feed to a noninhibiting species and comprises palladium and platinum, typically in a ratio of from 1 to 40 weight parts palladium per weight part platinum.

10 Claims, No Drawings

HYDROGENATION OF ACETYLENIC COMPOUNDS

FIELD OF THE INVENTION

This invention pertains to a process for effecting hydrogenation of acetylenic compounds to their paraffin counterparts.

BACKGROUND OF THE INVENTION

Palladium supported on carbon or alumina is typically used for the hydrogenation of acetylenic compounds to the corresponding paraffinic compounds. However, due to the presence of impurities in an acetylenics feed produced by the condensation of aldehydes or ketones with acetylene, the acetylenic compositions typically do not undergo complete hydrogenation. The feed impurities often prevent hydrogen of the olefin/paraffin bond while allowing hydrogen of the acetylene/olefin bond. Representative patents and literature which show the hydrogenation of acetylenic compounds are as follows:

U.S. Pat. No. 4,404,124 discloses a process for the hydrogenation of acetylene which is an admixture with ethylene. When producing polymer grade ethylene for the production of polyethylene, it is preferred that the acetylene content be reduced to a level below less than 5 ppm. The patent discloses the use of a co-catalyst of palladium and silver with the palladium constituting about 0.01 to 0.25 wt % of the catalyst. The catalyst is carried on an alumina support with the palladium concentrated at the surface of the support.

U.S. Pat. No. 4,831,200 discloses a process for the selective hydrogenation of alkynes and an alkene-rich hydrocarbon feed utilizing a palladium-based catalyst. The patent discloses in its prior art section, U.S. Pat. No. 4,493,906, the use of copper carried on a gamma alumina support. Group VIIIB metals, preferably palladium, is the catalyst most often used. The patentees report two problems are associated with the use of palladium as a catalyst, namely, that of hydrogenating 1,3-butadiene in the hydrocarbon feed and reduced catalyst life. Sequential hydrogenation first over palladium and then over copper is effective for enhancing catalyst life and minimizing butadiene hydrogenation.

U.S. Pat. No. 2,359,759 discloses a process for purifying olefinic compositions contaminated with acetylinic compounds, a wide variety of hydrogenation catalysts. The patentees report platinum, cobalt, reduced nickel, etc., may be employed to remote reaction between hydrogen and acetylenic byproducts, but reduced nickel and other metals are more useful, nickel alone for effecting the hydrogenation. A mixed catalyst comprising finely divided nickel and one or more metals selected from the group consisting of iron, copper, zinc and cobalt are alleged to display excellent activity in catalyst life.

U.S. Pat. No. 3,098,882 discloses a process for the hydrogenation of acetylene in admixture with olefinic compounds using a palladium catalyst impregnated with chromium. When the catalyst is carried on alumina, the activity of the palladium is reduced and the catalyst is stabilized against poisoning and inactivation.

U.S. Pat. No. 4,367,353 discloses a process for selectively hydrogenating ethylene into hydrocarbons utilizing a copper-containing catalyst containing a Group 8 metal or one containing vanadium, chromium, molybdenum, and tungsten.

U.S. Pat. No. 4,228,312 discloses a process for the hydrogenation of aromatic and acetylenic compounds utilizing a catalyst comprising a lithium metal coupled with a complex of rhodium halide and olefinic hydrocarbon ligand. In the prior art section of the reference, there is disclosed a process for the hydrogenation of aromatic hydrocarbons, e.g., benzene, utilizing a rhodium/silica catalyst as well as Group 8 metals including rhodium, ruthenium, platinum and palladium, and mixed catalysts of platinum/ruthenium; rhodium-ruthenium; platinum-palladium; palladium and rhodium and platinum and rhodium.

SUMMARY OF THE INVENTION

This invention pertains to an improved process for the hydrogenation of acetylenic compounds prepared by the condensation of ketones or aldehydes with acetylene wherein the acetylenic compounds are contacted with hydrogen in the presence of a hydrogenation catalyst under conditions for effecting hydrogenation. The improvement in the process resides in utilizing a novel cocatalyst system for hydrogenating the acetylenic compounds to paraffins. The cocatalyst converts the inhibiting impurity in the feed to a noninhibiting species and comprises palladium and platinum, typically in a ratio of from 1 to 40 weight parts palladium per weight part platinum.

Several advantages are associated with the process of this invention and these include:

an ability to effect a substantially complete hydrogenation of the acetylenic compound produced by the reaction of a ketone or aldehyde with acetylene and contaminated with impurities poisonous to palladium; and, an ability to effect hydrogenation of acetylenic compounds at excellent reaction rates; and an ability to utilize the catalyst system over an extended period of time without substantial deactivation.

DETAILED DESCRIPTION OF THE INVENTION

Acetylenic compounds typically are produced by reaction of aliphatic ketones and aldehydes with acetylene in the presence of potassium hydroxide. The resulting compounds are hydroxyl bearing, and a variety of alcohols and glycols may be produced. Representative aldehydes which can be reacted with acetylene to produce acetylenic compounds include the $C_{2-8}$ aliphatic ketones and $C_{2-8}$ aliphatic aldehydes. Examples of these ketones include acetone, 2-propanone, and methylisobutyl ketone. Aldehydes suited for producing acetylenic compounds include acetaldehyde, propionaldehyde, butyraldehyde, etc. Other examples of acetylenic compounds which are candidates for hydrogenation are described in U.S. Pat. Nos. 3,268,593, 2,985,689, 3,257,465 and U.S. Pat. No. 2,997,477; which are incorporated by reference.

Representative class of glycols and alcohols produced by the reaction of ketones with acetylene which lend themselves to the complete hydrogenation utilizing the catalyst system described above is represented below.

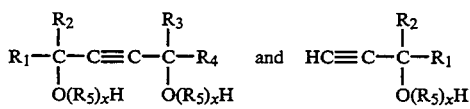

wherein $R_1$ and $R_4$ are hydrogen or $C_1$ to $C_4$ alkyl; $R_2$ and $R_3$ are hydrogen, alkyl, cycloalkyl or aryl, $R_5$ is alkylene oxide, and x is 0 or 1, preferably 1.

Examples of acetylenic glycols include 2,4,7,9-tetramethyl-5-decyne-4,7-diol; 4,7-dimethyl-5-decyne-4,7-diol; 2,3,6,7-tetramethyl-4-octyne-3,6-diol; 3,6-diethyl-4-octyne-3,6-diol; 2,5-dicyclopropyl-3-hexyne-2,5-diol; 3,6-dimethyl-4-octyne-3,6-diol; 2,5-diphenyl-3-hexyne-2,5-diol; 2,5-dimethyl-3-hexyne-2,5-diol; 5,8-dimethyl-6-dodecyne-5,8-diol.

Examples of acetylenic alcohols include 3-methyl-1-butyn-3-ol; 3-methyl-1-pentyn-3-ol; 3,5-dimethyl-1-hexyn-3-ol; 3-ethyl-5-methyl-1-heptyn-3-ol; 3-methyl-1-nonyn-3-ol; 3-ethyl-1-nonyn-3-ol and ethynyl cyclohexanol.

Ethoxylated derivatives of the above acetylenic glycols and acetylenic alcohols typically have from 1-30 ethylene oxide units, and preferably the sum of $R_5$ units is from 2-10. Such derivatives have use in ink and coating formulations.

The catalyst composition constituting the basis of the process improvement is a cocatalyst of palladium and platinum wherein the palladium is present in a proportion of 1 to 40 parts by weight per weight part of platinum. These metals typically are carried on a support, e.g., a refractory oxide, carbon, or alumina, with weight percentages of metal component based on the weight of the metal component and support from about 0.1 to 10%. The catalyst is utilized in the hydrogenation process in conventional amounts, e.g., from about 0.2 to 5% by weight of the acetylenic compound introduced as feedstock to the hydrogenation process.

Although not intending to be bound by theory, it is believed the function of platinum is to destroy or reduce any feed impurity in the feedstock, probably a ketone or a condensate of a ketone, which apparently becomes bound to the Pd/C catalyst and is not reduced. The competitive adsorption phenomenon inhibits the ability of the Pd/C catalyst to effect the hydrogenation of methylpent-yne-ol (MP) to an intermediate methylpentene-ol (MPE) to its saturated counterpart methylpentane-ol (MPS) and hydrogenation of dihydroxy-dimethylhexyne (DH) intermediate dihydroxydimethylhexene (DME) and then to its saturated counterpart dihydroxydimethylhexane (DHS) while allowing MP or MPE (or DH to DHE). The reduced impurity, probably an alcohol, will not compete for Pd/C sites and hence the reduction of MPE to MPS (or DNE to DNS) could proceed without interruption.

The traditional catalyst for the hydrogenation of acetylenes is palladium supported on either carbon or alumina. The function of the palladium is that of effecting hydrogenation of the acetylenic bond to form the olefin bond and the subsequent hydrogenation of the olefin bond to the single carbon bond. Palladium is an active catalyst and, in the absence of catalyst poison, e.g, condensates of ketones, etc., the palladium is effective for hydrogenating both the acetylenic bond to the olefin and the olefinic to bond single bonded carbon atoms. The problem associated with hydrogenating acetylenic compounds as described above is that impurities remain in the acetylenic compounds and these impurities tend to deactivate the palladium catalyst.

Conditions for effecting hydrogenation of the acetylenic compounds. The hydrogenation is carried out in a stirred reaction vessel at a temperature ranging from about 50° to 150° C. and from about 50 to 500 psig.

The following examples are provided to illustrate various embodiments of the invention and are not intended to limit the scope thereof.

COMPARATIVE EXAMPLE 1.

General Procedure

Examples 1–4 were carried out in an autoclave batch reactor. A one liter autoclave was charged with 400 g of acetylenic compound. To that preselected catalysts and amounts of catalyst were added, the autoclave sealed, purged with nitrogen and then with hydrogen. The autoclave was then pressurized with hydrogen to 100 psi and heated to a preselected temperature. At temperature, the autoclave pressure was maintained by addition of hydrogen from a ballast tank. When the reaction was completed, the autoclave was cooled. The reaction products were analyzed by GC. The percent of each compound is expressed as area percent.

Hydrogenation of Acetylenic Compounds using Palladium on Carbon

Four hundred grams of 3-methyl-pent-yne-3-ol (MP) was hydrogenated at 100° C. and 100 psi hydrogen pressure in the presence of 3.2 g of 5% Pd/C catalyst. The catalyst was base modified by adding 8 g of 10% sodium bicarbonate solution. As seen in Table 1, the hydrogenation ceased after the consumption of approximately the first molar equivalent of hydrogen. The reaction temperature was increased from 100° C. to 160° C. for an additional 30 min with no further consumption of hydrogen being seen. Table 1 sets forth the conditions and results.

TABLE 1

Hydrogenation of MP
Temp 100-160° C., 100 psi hydrogen pressure
5% Pd/C Catalyst[a] and NaHCO$_3$.

| Feed | MP | MPE[b] | MPS | Unk[d] Low | Unk[c] High |
|---|---|---|---|---|---|
| Feed MP[e] | 99.2 | 0 | 0 | 0.8 | 0 |
| Hydrogenated Reaction Product[f] | 0 | 82.0 | 2.70 | 1.60 | 13.70 |

[a]Commercially available 5% Pd on Carbon Catalyst
[b]3-methylpent-ene-3-ol
[c]All unknown impurities and byproducts seen after MPS in GC analysis.
[d]All unknown impurities and byproducts seen before MPS in GC analysis.
[e]MP was produced by the condensation of methylethylketone with acetylene followed by distillation.
[f]45 min at 100° C. and 30 min at 160° C.

As can be observed from the above Table 1, there was difficulty in effecting complete hydrogenation of 3-methyl-pent-yne-3-ol (MP) to its saturated counterpart 3-methyl-pentane-3-ol (MPS) utilizing Pd/C as a catalyst. After the consumption of about i molar equivalent of hydrogen the reaction stopped. Raising the temperature after 45 minutes' reaction to 160° C. did not result in further hydrogen consumption. It was concluded that the catalyst was ineffective for reducing the olefin, 3-methyl-pent-ene-3-ol (MPE) generated on hydrogenation of the 3-methyl-pent-yne-3-ol even at the higher temperature.

EXAMPLE 2

Hydrogenation of MPE

Four hundred grams of 3-methyl-pent-yne-3-ol (MP) was hydrogenated at 100° C. and 100 psi hydrogen pressure in the presence of 3.2g of 5% Pd/C catalyst. The catalyst was base modified by adding 8g of 10% sodium bicarbonate solution. A reaction mixture obtained similar to Example 1 was cooled to room temperature and a sample was taken for analysis. As shown in Table 2, the run being designated MPS-2, hydrogenation ceased after the consumption of about 1 molar equivalent of hydrogen.

To the remaining mixture of the Run designated MPS-2 containing the Pd/C catalyst was added 0.1 g of Pt/C catalyst and the reaction mixture reheated to 80° C. A total pressure of 100 psi was maintained. Hydrogenation of the MPE commenced immediately and was completed in 20 min. This run was designated MPS-3. The conditions and analysis of that sample are given in Table 2 following Example 3.

EXAMPLE 3

Study of Catalyst Life

In order to investigate catalyst life the mixed Pd/Pt catalyst utilized in run MPS-3 of Example 2 was recovered from the reaction product of Example 2 and the procedure of Example 2 repeated with new feedstock for an additional three batches (400 g×3) to produce 1.6 Kg of MPS from MP. These runs were designated MPS-4, MPS-5 and MPS-6. The run designated MPS-7 was carried out in accordance with the general procedure of Example 2 except that the catalyst was platinum on carbon. The conditions and analysis of these products for Examples 2 are set forth in Table 2. All catalyst weights are given on dry basis.

EXAMPLE 4

Effect of Catalyst, Temperature and Pressure

The general procedure of Example 2 was repeated except that the levels of catalyst, temperature, and pressure was varied in order to show the impact of temperature, pressure and the catalyst loading. Table 3 sets forth reaction conditions and results.

TABLE 3

Hydrogenation of MP with physical mixture of Pd/Pt catalyst
Hydrogenation of 125 g MP in a 300 cc autoclave batch reactor using a physical mixture of 5% Pd/C[a] and 5% Pt/C[a] (Pd:Pt = 10:1) and 2.5 gms 10% sodium bicarbonate solution.

| Run | Reaction Time | MP | MPE[b] | MPS | Unk[d] Low | Unk[c] High |
|---|---|---|---|---|---|---|
| Feed MP[e] | — | 99.2 | 0.0 | 0.0 | 0.8 | 0.0 |
| MPS-1 | 155 min | 0.0 | 0.0 | 94.9 | 0.4 | 4.7 |
| MPS-2 | 330 min | 0.0 | 0.0 | 95.0 | 0.5 | 4.5 |
| MPS-3 | 130 min | 0.0 | 0.0 | 93.0 | 0.9 | 6.1 |

[a]All catalyst weights are on dry basis and are commercially available.
[b]Same as Table 1.
[c]Same as Table 1.
[d]Same as Table 1.
[e]Same as Table 1.
MPS-1: 20 psi total pressure, 80° C.; 0.45 g of 5% Pd/C + 0.045 g of 5% Pt/C
MPS-2: 20 psi total pressure, 80° C.; 0.225 g of 5% Pd/C + 0.023 g of 5% Pt/C
MPS-3: 20 psi total pressure, 120° C.; 0.45 g of 5% Pd/C + 0.045 g of 5% Pt/C.

With the utilization of the palladium/platinum cocatalyst as set forth in Runs MPS-1 to MPS-3 of Table 3, the hydrogenation can be effected at low reactor pressure (20 psi) and at low catalyst loading. The effect of temperature is that higher temperatures favor faster reaction rates.

EXAMPLE 5

Hydrogenation of 2,5-dihydroxy-2,5-dimethyl-hex-3-yne (DH)

The acetylenic glycol, 2,5-dihydroxy-2,5-dimethyl

TABLE 2

Hydrogenation of MP at 100 psi hydrogen pressure

| Feed/Product | Catalyst | Reaction Time (min) | MP | MPE[b] | MPS | Unk[d] Low | Unk[c] High |
|---|---|---|---|---|---|---|---|
| Feed MP[e] | | | 99.2 | 0.0 | 0.0 | 0.8 | 0.0 |
| Run | | | | | | | |
| MPS-2 | 3.2 g of 5% Pd/C[a] + 8 g of 10% sodium bicarbonate | 45 min 80° C. + 30 min at 160° C. | 0.2 | 90.1 | 4.9 | 0.7 | 4.1 |
| MPS-3 | Cat MPS-2 + 0.1 g of 5% Pt/C[a] | 20 min at 80° C. | 0.0 | 0.0 | 94.8 | 0.9 | 4.3 |
| MPS-4 | Catalyst MPS 3 | 45 min at 80° C. | 0.8 | 2.4 | 92.5 | 0.7 | 3.6 |
| MPS-5 | Catalyst MPS 4 | 40 min at 80° C. | 0.7 | 7.0 | 88.6 | 0.4 | 3.3 |
| MPS-6 | Catalyst MPS 5 | 40 min at 80° C. | 0.5 | 0.2 | 93.5 | 1.0 | 4.8 |
| MPS-7 | 0.1 g of 5% Pt/C[a] catalyst | 60 min at 100° C. | No hydrogen consumption. | | | | |

[a]Commercial catalyst
[b]Same as Table 1
[c]Same as Table 1
[d]Same as Table 1
[e]Same as Table 1

The results show that the run MPS-2 consisting of Pd/C as the catalyst was ineffective, but when combined with Pt/C in Runs MPS-3 to MPS-6, excellent conversion to MPS was achieved. Run MPS-7 which utilized on Pt/C as the sole catalyst was ineffective for hydrogenating the methyl-pent-yn ol to its olefin and saturated counterparts. These data show the synergistic effect of Pd and Pt.

hex-3-yne (DH), is produced by condensation of acetone and acetylene followed by distillation. DH was hydrogenated to 2,5-dihydroxy-2,5-dimethyl hexane (DHS) in a 300 cc autoclave reactor. The reactor was charged with 125 g of DH, 1 g of 5% Pd/C catalyst (dry basis) and 0.8 g 10% sodium bicarbonate solution. The autoclave was sealed, purged with nitrogen followed by hydrogen and then pressurized with hydrogen to 100 psig total pressure. The autoclave was then heated to 140°–160° C. with addition of hydrogen from the ballast tank as needed to maintain 100 psig pressure.

If the DH purity is high (>98%) the reaction proceeded smoothly and completes the hydrogenation in about 150–200 min. A DHS purity of 99+% is required for most applications, the major impurity being 2,5 dihydroxy 2,5 dimethyl hex-3-ene (DHE). Table 4 gives an example of a run with DH of high purity (99%) and also a run with DH of low purity (95%). With the low purity DH, often the reaction stops or ceases to consume hydrogen after about one molar equivalent of hydrogen is consumed. The runs in Table 4 show that with a small amount of 5% Pt/C catalyst the reaction can be made to go to completion. The product without any unsaturates could be easily separated by distillation.

TABLE 4

Hydrogenation of 125 g of DH in a 300 cc Autoclave Reactor Using 5% Pd/C Catalyst and 0.8 gms 10% Sodium Bicarbonate Solution.

| Run | Temp °C. | Press PSI | DH | DHE | DHS | DMH-OL[c] | Impurities/ Byproducts | React Time |
|---|---|---|---|---|---|---|---|---|
| Feed a | — | — | 99.1 | 0 | 0 | 0 | 0.9 | — |
| 1. Feed a (1 g 5% Pd/C[b] | 140 | 80 | 0 | 0 | 98.1 | 0.9 | 1.0 | 180 mi |
| 2. Feed b | — | — | 95.1 | 0 | 0 | 0 | 4.9 | — |
| 3. Feed b 1 g 5% Pd/C[b] | 160 | 100 | 0 | 61.5 | 22.1 | 8.9 | 7.5 | After 60 min the hydrogen consumption ceased. |
| 4. Run 3 add 0.1 gms of 5% Pt/C Catalyst | 160 | 100 | 0 | 0 | 82.7 | 11.2 | 6.1 | 60 min |

[a]DH produced by condensation of acetone with acetylene.
[b]All catalysts weights are on dry basis and were purchased from a commercial source.
[c]2,5-dimethylhexane-2-ol The role of the Pt/C catalyst in Run 4 was to destroy or reduce the feed impurity, probably a ketone, which was apparently bound to Pd/C catalyst. It was not reduced. Apparently, this competitive adsorption phenomenon prevents the Pd/C catalyst to effect the hydrogenation of DHE to DHS while allowing DH to DHE (or MP to MPE). The reduced impurity, probably an alcohol, probably does not compete for Pd/C hydrogenation sites and therefore, the reduction of MPE to MPS (or DHE to DHS) proceeds without interruption.

What is claimed is:

1. In a process for the hydrogenation of acetylenic compounds prepared by the condensation of ketones or aldehydes with acetylene wherein the acetylenic compounds contain impurities poisonous to palladium and are contacted with hydrogen in the presence of a hydrogenation catalyst under conditions for effecting hydrogenation, the improvement which resides in utilizing a cocatalyst system for hydrogenating the acetylenic compounds to corresponding fully hydrogenated compounds which comprises palladium and platinum.

2. The process of claim 1 wherein the palladium and platinum are present in a ratio of from 1 to 40 weight parts palladium per weight part platinum.

3. The process of claim 2 wherein the acetylenic compounds are represented by the formulas:

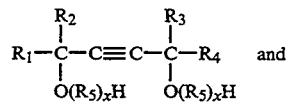

I

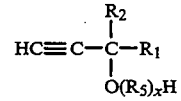

II wherein $R_1$ and $R_4$ are hydrogen or $C_1$ to $C_4$ alkyl; $R_2$ and $R_3$ are hydrogen, alkyl, cycloalkyl or aryl, $R_5$ is alkylene oxide, and x is 0 or 1.

4. The process of claim 3 wherein $R_1$ and $R_2$ are methyl.

5. The process of claim 4 wherein $R_3$ and $R_4$ are methyl.

6. The process of claim 3 wherein $R_5$ is hydrogen.

7. The process of claim 6 wherein the acetylenic compound is represented by the Formula I.

8. The process of claim 7 wherein x is 1.

9. The process of claim 3 where $R_2$ is ethylene oxide and the acetylenic compound is represented by Formula I.

10. The process of claim 9 wherein $R_5$ is from 2–10 ethylene oxide units.

* * * * *